United States Patent [19]

Schneider

[11] Patent Number: 4,761,408

[45] Date of Patent: Aug. 2, 1988

[54] CRYSTALLINE AMINOMETHYL COMPOUND

[75] Inventor: Peter Schneider, Bottmingen, Switzerland

[73] Assignee: Ciba-Geigy Corporation, Ardsley, N.Y.

[21] Appl. No.: 792,076

[22] Filed: Oct. 28, 1985

[30] Foreign Application Priority Data

Nov. 2, 1984 [CH] Switzerland ............... 5266/84

[51] Int. Cl.$^4$ .................. C07D 499/00; A61K 31/425
[52] U.S. Cl. ..................... 514/192; 540/310
[58] Field of Search ............... 260/245.2 R; 540/310; 514/210

[56] References Cited

U.S. PATENT DOCUMENTS

| | | | |
|---|---|---|---|
| 4,272,437 | 6/1981 | Menand | 260/239.1 |
| 4,347,183 | 8/1982 | Afonso | 260/245.2 R |
| 4,386,030 | 5/1983 | Christensen et al. | 260/245.2 R |
| 4,540,580 | 9/1985 | Afonso et al. | 540/310 |
| 4,634,556 | 1/1987 | Jenkins et al. | 540/310 |
| 4,656,165 | 4/1987 | Lang | 540/310 |

FOREIGN PATENT DOCUMENTS

| | | |
|---|---|---|
| 0003960 | 9/1979 | European Pat. Off. . |
| 013662 | 7/1980 | European Pat. Off. . |
| 0070204 | 1/1983 | European Pat. Off. . |
| 0069373 | 1/1983 | European Pat. Off. . |
| 846832 | 4/1985 | South Africa . |
| 2043639 | 10/1980 | United Kingdom . |

OTHER PUBLICATIONS

Canad. J. Chem. 62: pp. 2282–2286 (1984).
Tetrahedron Letters 22 (36): pp. 3485–3488 (1981).
CA: 56:166194 (1980) (Japanese).

*Primary Examiner*—Nicholas S. Rizzo
*Attorney, Agent, or Firm*—Irving M. Fishman

[57] ABSTRACT

The invention relates to (5R,6S)-2-aminomethyl-6-[(1R)-1-hydroxyethyl]-2-penem-3-carboxylic acid in crystalline form and a process for the manufacture thereof. The substance is suitable for treating infectious diseases.

12 Claims, No Drawings

CRYSTALLINE AMINOMETHYL COMPOUND

The invention relates to (5R,6S)-2-aminomethyl-6-[(1R)-1-hydroxyethyl]-2-penem-3-carboxylic acid in crystalline form, processes for the manufacture thereof, and pharmaceutical preparations containing this compound.

German Offenlegungsschrift No. 2 950 898 describes racemic (5R,6S,1'R and 5S,6R,1'S)-2-aminomethyl-6-(1'-hydroxyethyl)-2-penem-3-carboxylic acid, a process for its manufacture and its use as an antibacterial agent. The racemic compound is obtained in the form of an amorphous substance upon working up.

Amorphous substances have various disadvantages which make them seem not very suitable, or even unsuitable, for use, especially for the manufacture of pharmaceutical preparations. One disadvantage is the relatively large surface area of the amorphous substances as compared with crystallised substances, and this, in conjunction with the irregular thermo-dynamically unfavourable arrangement of the molecules in the solid form, is responsible for a considerably greater susceptibility to external influences, such as air, light and elevated temperature. In addition, amorphous substances have a far greater tendency than do crystallised compounds to occlude solvents and stubbornly to resist the release of these impurities, for example during drying. Preparations containing such impurities, especially toxic solvents such as acetone or methanol, are not suitable for use in medicine, especially in the case of parenteral administration. A further disadvantage of amorphous products is that they absorb atmospheric moisture to a considerably greater extent than do crystalline products. The increasing water content of such products on the one hand renders more difficult the manufacture of pharmaceutical preparations having a constant content of active ingredient and, moreover, it has an adverse effect on the flowability of the product. Amorphous products have a relatively large bulk volume which can make it necessary to use larger vessels for storage and for the manufacture of medicament preparations. The often unsatisfactory solubility of amorphous products (these products easily form lumps or stick together, which reduces the rate at which they dissolve) should also be mentioned in this connection.

In view of the mentioned disadvantages of amorphous products, especially the low stability to storage, it would seem desirable to find a form other than the amorphous form which has the properties required of the active ingredient of a medicament, such as, especially, good stability to storage and constant weight.

It has now been found that, in addition to advantages attributable to its crystalline state, crystalline, optically active (5R,6S)-2-aminomethyl-6-[(1R)-1-hydroxyethyl]-2-penem-3-carboxylic acid has surprising pharmacological properties.

The invention accordingly relates to (5R,5S)-2-aminomethyl-6-[(1R)-1-hydroxyethyl]-2penem-3-carboxylic acid in crystalline form.

The term "crystalline" is to be understood as meaning that the product is substantially free of amorphous constituents.

The invention relates especially to crystalline (5R,6S)-2-aminomethyl-6-[(1R)-1-hydroxyethyl]-2-penem-3-carboxylic acid characterised by the following lattice spacings (d-values) and relative line intensities of its X-ray powder pattern (camera according to Guinier, radiation source: copper-$K_{\alpha 1}$):

| d-values (Ångstrom) | relative intensity |
| --- | --- |
| 10.9 | very strong |
| 10.0 | medium |
| 9.7 | medium |
| 7.9 | strong |
| 7.3 | strong |
| 7.0 | strong |
| 6.7 | weak |
| 6.3 | very strong |
| 5.90 | very weak |
| 5.85 | very weak |
| 5.60 | very weak |
| 5.53 | very weak |
| 5.44 | very weak |
| 5.33 | very weak |
| 5.01 | very weak |
| 4.93 | weak |
| 4.64 | very weak |
| 4.58 | very weak |
| 4.53 | strong |
| 4.42 | very weak |
| 4.34 | very strong |
| 4.28 | very weak |
| 4.23 | very weak |
| 4.10 | strong |
| 4.05 | very weak |
| 3.99 | medium |
| 3.91 | weak |
| 3.82 | medium |
| 3.78 | medium |
| 3.73 | strong |
| 3.65 | medium |
| 3.59 | strong |
| 3.54 | medium |
| 3.42 | strong |
| 3.36 | medium |
| 3.29 | strong |
| 3.20 | medium |
| 3.13 | medium |
| 3.11 | strong |
| 3.03 | medium |
| 3.00 | medium |

Crystalline (5R,6S)-2-aminomethyl-6-[(1R)-1-hydroxyethyl]-2-penem-3-carboxylic acid contains per mol approximately from 0.2 to 1.5 mol of water. Since it has been established that the effect of the changing water content on the X-ray powder pattern is only negligible (the lattice spacings remain constant and the estimated line intensities vary only very slightly), it must be assumed that the water is not part of the crystal lattice but is bound more or less loosely in the crystal structure. A defined hydrate does not therefore exist.

The product has good crystallinity, is very stable even under the relatively long-term action of light, heat (50° C.) and air and, under approximately normal ambient conditions, shows no tendency to absorb relatively large quantities of water from the air. Its stability to storage can therefore be described as good. In comparison with the previously known, amorphous racemic 2-aminomethyl-6-[(1R)-1-hydroxyethyl]2-penem-3-carboxylic acid, the product according to the invention has a higher degree of purity and, in addition, does not need to be lyophilised in order to separate off solvent residues, but can be further processed after customary drying in vacuo. After grinding the crystals, the crystalline product can be converted into a mechanically pourable, that is to say flowable, form without any loss of stability and can be processed in the desired quantities without difficulty to form parenterally administrable medicament preparations that are stable to storage.

The crystalline (5R,6S)-2-aminomethyl-6-[(1R)-1hydroxyethyl]-2-penem-3-carboxylic acid according to the invention has surprising pharmacological properties. For example it is effective in vitro against gram-positive and gram-negative cocci, for example *Staphylococcus aureus, Streptococcus pyogenes, Streptococcus pneumoniae, Streptococcus faecalis, Neisseria meningitidis* and *Neisseria gonorrhoeae*, against enterobacteria, for example *Escherichia coli, Proteus mirabilis* and *Klebsiella pneumoniae*, against *Haemophilus influenzae, Pseudomonas aeruginosa* and anaerobic bacteria, for example *Bacteroides sp.*, and *Clostridium sp.*, in minimum concentrations of from approximately 0.05 to approximately 8 μg/ml. In vivo, in the case of the systemic infection of mice, for example by *Staphylococcus aureus, Escherichia coli* or *Streptococcus pyogenes*, $ED_{50}$ values of from approximately 0.3 to approximately 30 mg/kg are obtained on parenteral, such as subcutaneous, administration.

In comparison with the amorphous, racemic (1′R,5R,6S+1′S,5S,6R)-2-aminomethyl-6-(1′-hydroxyethyl)-2-penem-3-carboxylic acid (compound B) previously known from U.S. Pat. No. 4,272,437, crystalline (5R,6S)-2-aminomethyl-6-[(1R)-1-hydroxyethyl]-2-penem-3-carboxylic acid (compound A) has the following superior action in vitro:

TABLE 1

Antibiotic activity of (5R,6S)-2-aminomethyl-6-[(1R)-1-hydroxyethyl]-2-penem-3-carboxylic acid and the previously known, comparison compound B in vitro

| Microorganism | in vitro MIC (μg/ml) | |
|---|---|---|
| | Compound A | Compound B |
| *Staphylococcus aureus* 10 B | 0.05 | 0.1 |
| *Staphylococcus aureus* 2999i + p + | 0.05 | 0.2 |
| *Staphylococcus aureus* A 124 | 0.1 | 0.2 |
| *Staphylococcus aureus* Wood 46 | 0.05 | 0.1 |
| *Streptococcus pyogenes* Aronson 1129 | 0.2 | 0.5 |
| *Streptococcus pneumoniae* III/84 | 0.1 | 0.2 |
| *Neisseria meningitidis* 1316 | 0.5 | 1 |
| *Neisseria gonorrhoeae* 1317/4 | 0.5 | 1 |
| *Haemophilus influenzae* NCTC 4560 | 1 | 2 |
| *Escherichia coli* 205 | 2 | 8 |
| *Escheichia coli* 205 R + TEM | 4 | 8 |
| *Escherichia coli* 16 | 4 | 8 |
| *Escherichia coli* 2018 | 2 | 4 |
| *Escherichia coli* UB 1005 | 4 | 16 |
| *Escherichia coli* DC2 | 8 | 16 |
| *Escherichia coli* B-1385 | 4 | 8 |
| *Klebsiella pneumoniae* 327 | 2 | 4 |
| *Serratia marcescens* 344 | 4 | 8 |
| *Enterobacter cloacae* P 99 | 4 | 8 |
| *Enterobacter cloacae* ATCC 13047 | 4 | 16 |
| *Proteus mirabilis* 774 | 1 | 4 |
| *Proteus mirabilis* 1219 | 2 | 8 |
| *Proteus rettgeri* 856 | 0.5 | 1 |
| *Proteus morganii* 2359 | 0.5 | 2 |
| *Proteus morganii* 1518 | 2 | 4 |
| *Pseudomonas aeruginosa* ATCC 12055 | 0.05 | 0.1 |
| *Pseudomonas aeruginosa* K 799/61 | 0.1 | 0.2 |
| *Pseudomonas aeruginosa* 143738R | 0.5 | 2 |
| *Clostridium perfringens* | 2 | 4 |
| *Bacteroides fragilis* 01 | 0.5 | 1 |

As compared with the corresponding previously known amorphous racemate (compound B), the crystalline compound A according to the invention has a higher activity in all the strains tested by a factor of from 2 to 4.

Compounds A and B have the following stability (expressed in half-life periods $t_{\frac{1}{2}}$) to the enzyme dehydropeptidase from human kidneys:

| | $t_{\frac{1}{2}}$(hours) |
|---|---|
| Compound A | 6.75 |
| Compound B | 2.20 |

Compared with the previously described amorphous racemate (compound B) the crystalline compound A according to the invention has, surprisingly, a considerably greater half-life under the action of renal dehydropeptidase.

Crystalline (5R,6S)-2-aminomethyl-6-[(1R)-1-hydroxyethyl]-2-penem-3-carboxylic acid can therefore be used in the form of a parenterally administrable antibacterial antibiotic, for example in the form of suitable pharmaceutical preparations, for the treatment of infections.

The invention also relates to a process for the manufacture of crystalline (5R,6S)-2-aminomethyl-6-[(1R)-1-hydroxyethyl]-2-penem-3-carboxylic acid. Surprisingly, it has been found that the crystalline product can be obtained by causing (5R,6S)-2-aminomethyl-6-[(1R)-1-hydroxyethyl]-2-penem-3-carboxylic acid to crystallise from a supersaturated solution in a water-containing organic solvent, and then isolating and drying the product.

A solution of (5R,6S)-2-aminomethyl-6-[(1R)-1-hydroxyethyl]-2-penem-3-carboxylic acid in a water-containing organic solvent is to be understood, for example, as being a solution in a solvent mixture consisting of water and a suitable, water-miscible organic solvent. As organic solvents there come into consideration, especially, alcohols, such as lower alkanols having from 1 to 4 carbon atoms, for example methanol, ethanol, n-propanol, isopropanol, n-butanol, 2-butanol and sec.-butanol, glycols having from 1 to 4 carbon atoms, for example ethylene glycol, and the mono- and di-($C_1$-$C_2$)-alkyl ethers thereof, for example ethylene glycol monomethyl ether, ethylene glycol dimethyl ether and ethylene glycol monoethyl ether. A solvent mixture consisting of water and the water-miscible organic solvent has, for example, a water content of from 2 to 20%, especially of from 2 to 10%. Preferred are aqueous-alcoholic solutions, such as, especially, aqueous-ethanolic, aqueous-propanolic and aqueous-butanolic, such as aqueous-2-butanolic, solutions, having a water content of from 2 to 10%.

A supersaturated solution can be manufactured by dissolving any form of (5R,6S)-2-aminomethyl-6-[(1R)-1-hydroxyethyl]-2-penem-3-carboxylic acid, for example the amorphous form or mixtures of the amorphous and the crystalline form, in a mixture of water and one of the above-mentioned organic solvents at room temperature or at elevated temperature, for example up to the boiling point of the solvent used, but preferably up to a maximum of 50° C., avoiding or removing any crystallisation seeds, and bringing the resulting pure solution into a state of supersaturation, as described hereinafter. For this purpose the compound is preferably dissolved in water and then the organic solvent is added. It is also possible, however, to use a previously prepared mixture of water and the organic solvent and to dissolve the (5R,6S)-2-aminomethyl-6-[(1R)-1-hydroxyethyl]-2-penem-3-carboxylic acid therein, optionally while heating, for example up to the boiling point of the mixture, but preferably to a maximum of 50° C. During the course of crystallisation or beforehand, some of the solvent or solvent mixture can be distilled off in order to increase the degree of supersaturation.

The supersaturated solution can be obtained, for example, by cooling a saturated or almost saturated solution of the compound, which may be warm, that is to say at a temperature of from approximately 20° to approximately 50° C., and which is free of any crystallisation seeds, until supersaturation takes place, for example to from approximately 0° to approximately 20° C., or by removing some of the solvent or solvent mixture by distillation. The cooling operation is preferably carried out slowly, while stirring.

Crystal formation may occur spontaneously, for example at the surface of the reaction vessel or stirring apparatus, but can also be initiated by inoculation, that is to say the introduction of seed crystals. If no seed crystals are available, they can be manufactured in customary manner, advantageously in an aliquot portion of the solution, for example by means of vigorous shaking, the introduction of powdered glass, or scratches on the vessel wall. It is, however, also possible to supercool the whole solution slightly, that is to say by a few degrees, for example from 2° to 5° C., in order to promote spontaneous crystal formation, and then to heat it to the starting temperature again.

The crystalline compound can also be manufactured by digesting the amorphous compound in a solvent mixture in which it is only sparingly soluble, such as in one of the mentioned organic solvents having a low water content, such as in one of the mentioned lower alkanols having a water content of from 2 to 10%, for example in 90% to 98% ethanol, at room temperature or at slightly elevated or reduced temperature, for example at from 15° to 25° C., while stirring. During this process, the amorphous form is converted into the crystalline form. The conversion is as a rule complete after approximately from 20 to 30 minutes, with the result that the digesting can be interrupted after this period of time, and at the latest after approximately 60 minutes.

The novel crystalline compound that is formed can be isolated and collected with the aid of any available method of separating binary solid/liquid systems, for example by filtration, pressure filtration (filtration with suction), centrifugation or decanting. In order to remove impurities in remaining mother liquor residues, the residues can be washed with water or with the pure solvent mixture used for crystallisation.

Drying is effected at normal or slightly elevated temperature, for example in a temperature range of from approximately 15° C. to approximately 40° C., preferably at from approximately 20° to approximately 25° C. (room temperature), and is continued until the weight is approximately constant. In order to accelerate drying, the operation can be carried out under reduced pressure, it being possible to use, for example, a so-called water-jet vacuum (from approximately 650 to approximately 3300 Pa) or a high vacuum (from approximately 5 to approximately 100 Pa).

The starting material, amorphous (5R,6S)-2-aminomethyl-6-[(1R)-1-hydroxyethyl]-2-penem-3-carboxylic acid, is not yet known and can be manufactured as follows: in a compound of the formula

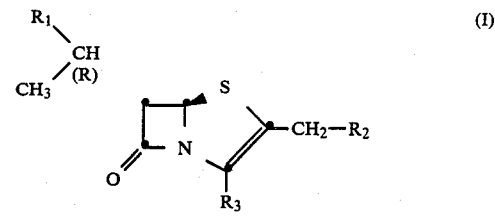

in which $R_1$ is a protected hydroxy group, $R_2$ is a protected amino group and $R_3$ represents a protected carboxy group, the protected functional groups are converted into the free functional groups.

A protected hydroxy group $R_1$ is, for example, tri-$(C_1-C_4)$-alkylsilyloxy, for example trimethylsilyloxy or tert.-butyldimethylsilyloxy, halogen-$(C_1-C_4)$alkoxycarbonyloxy, in which halogen is, for example, chlorine or bromine, for example 2-bromo- or 2,2,2-trichloro-ethoxycarbonyloxy, or $(C_1-C_4)$-lower alkenyloxycarbonyloxy optionally substituted by halogen, such as chlorine or bromine, for example allyloxycarbonyloxy or 2-chloroallyloxycarbonyloxy.

A protected amino group $R_2$ is, for example, azido, phthalimido, $(C_1-C_4)$-lower alkenyloxycarbonylamino optionally substituted by halogen, such as chlorine or bromine, for example allyloxycarbonylamino or 2-chloroallyloxycarbonylamino, or benzyloxycarbonylamino optionally substituted by nitro, for example p-nitrobenzyloxycarbonylamino.

A protected carboxy group $R_3$ is, for example, benzyloxycarbonyl optionally substituted by nitro, for example p-nitrobenzyloxycarbonyl, $(C_1-C_4)$-lower alkenyloxycarbonyl optionally substituted by halogen, such as chlorine or bromine, for example allyloxycarbonyl or 2-chloroallyloxycarbonyl, or ethoxycarbonyl substituted in the 2-position by cyano or tri-$(C_1-C_4)$-lower alkylsilyl, for example di-n-butylmethyl or trimethylsilyl.

The protecting groups can be removed in stages or simultaneously. Preferred is the embodiment in which all three protecting groups are removed in one step, that is to say simultaneously.

The removal of the protecting groups is effected according to processes known per se. For example a hydroxy group $R_1$ protected by tri-$(C_1-C_4)$-alkylsilyl and ethoxycarbonyl $R_3$ substituted in the 2-position by tri-$(C_1-C_4)$-lower alkylsilyl can be converted into the free hydroxy group $R_1$ and into the free carboxy group $R_3$, respectively, for example by treatment with a salt of hydrofluoric acid that yields fluoride anions, such as an alkali metal fluoride, for example sodium fluoride, in the presence of a macrocyclic polyether (Crown ether) or with the fluoride of an organic quaternary base, such as tetra-$(C_1-C_4)$-alkylammonium fluoride, for example tetraethylammonium fluoride. Halogen-$(C_1-C_4)$alkoxycarbonyloxy $R_1$, azido $R_2$, optionally nitrosubstituted benzyloxycarbonylamino $R_2$ or benzyloxycarbonyl $R_3$ can be converted into free hydroxy $R_1$, free amino $R_2$ and into free carboxy $R_3$, respectively, by reduction, for example by catalytic hydrogenation with hydrogen in the presence of a suitable hydrogenation catalyst, for example platinum oxide or palladium. The conversion of an amino group $R_2$ protected in the form of a phthalimido group into free amino $R_2$ is effected, for example, by reaction with hydrazine. An ethoxycarbonyl group $R_3$ substituted in the 2-position by cyano can be converted into free carboxy $R_3$, for example by treatment with a basic agent, for example an alkali metal hydroxide or carbonate, such as sodium or potassium carbonate.

In a preferred embodiment of the process, $R_1$ represents $(C_1-C_4)$-lower alkenyloxycarbonyloxy, especially allyloxycarbonyloxy, $R_2$ represents $(C_1-C_4)$-lower alkenyloxycarbonylamino, especially allyloxycarbonylamino, and $R_3$ represents $(C_1-C_4)$-lower alkenyloxycarbonyl, especially allyloxycarbonyl. The choice of the preferred, especially allyl-containing, protecting groups mentioned allows all three functional groups to be freed in one step.

The process for the simultaneous conversion of a $(C_1-C_4)$-lower alkenyloxycarbonyloxy group $R_1$ into hydroxy, a $(C_1-C_4)$-lower alkenyloxycarbonylamino group $R_2$ into amino and a $(C_1-C_4)$-lower alkenyloxycarbonyl group $R_3$ into carboxy, lower alkenyl representing especially allyl, is characterised in that a compound of the formula I is reacted with a lower alkenyl group acceptor in the presence of tetrakis-triphenylphosphinepalladium and optionally in the presence of triphenylphosphine.

Suitable acceptors for lower alkenyl groups, such as especially the allyl group, are, for example, amines, such as especially sterically hindered amines, for example tert.-butylamine, also tri-$(C_1-C_4)$-lower alkylamines, for example triethylamine, morpholine or thiomorpholine, aliphatic or cycloaliphatic β-dicarbonyl compounds, for example acetylacetone, ethyl acetoacetate or dimedone, and also $(C_2-C_4)$-lower alkanecarboxylic acids, for example acetic acid or propionic acid. The preferred acceptor is dimedone.

The reaction is carried out using from 1.5 to 10 molar equivalents of the lower alkenyl group acceptor in the presence of from 2 to 10 mol %, especially from 5 to 8 mol % (based on the starting compound of the formula I), of tetrakis-triphenylphosphine-palladium catalyst, and optionally in the presence of up to 50 mol % of triphenylphosphine in an inert solvent, such as an ether, for example dioxan or especially terahydrofuran, a halohydrocarbon, for example methylene chloride, a lower alkanol, for example ethanol, an ester, for example ethyl acetate, or in a mixture thereof at room temperature or at somewhat elevated or reduced temperature, for example at from approximately 0° to approximately 40° C., preferably at room temperature, if necessary in an inert gas atmosphere, such as in a nitrogen or argon atmosphere. (5R,6S)-2-aminomethyl-6-[(1R)-1-hydroxyethyl]-2-penem-3-carboxylic acid separates out from the reaction mixture in the form of an amorphous precipitate.

When using dimedone as the lower alkenyl group acceptor and tetrahydrofuran as the solvent, (5R,6S)-2-aminomethyl-6-[(1R)-1-hydroxyethyl]-2-penem-3-carboxylic acid separates out in a surprisingly highly pure form (degree of purity greater than 90%) with the result that after decolouring with activated carbon the product can be subjected directly to the crystallisation process without further purifying steps, such as column chromatography and the like, being necessary.

The invention also relates to the process for the manufacture of (5R,6S)-2-aminomethyl-6-[(1R)-1-hydroxyethyl]-2-penem-3-carboxylic acid from the compounds of the formula I.

The starting compounds of the formula I can be manufactured according to processes known per se, for example according to the process described in European Patent Application No. 82 113 or in German Offenlegungsschrift No. 3224055.

The invention also relates to pharmaceutical preparations containing a therapeutically effective amount of crystalline (5R,6S)-2-aminomethyl-6-[(1R)-1-hydroxyethyl]-2-penem-3-carboxylic acid together with or in admixture with inorganic or organic, solid or liquid, pharmaceutically acceptable carriers that are suitable for parenteral, that is to say, for example, intramuscular, intravenous, subcutaneous or intraperitoneal, administration.

Suitable for parenteral administration are especially infusion solutions, preferably isotonic aqueous solutions or suspensions, it being possible for these to be manufactured before use, for example from preparations that contain the active ingredient alone or together with a carrier, for example mannitol. Such preparations can be sterilised and/or contain adjuncts, for example preservatives, stabilisers, wetting agents and/or emulsifiers, solubilisers, salts for regulating the osmotic pressure and/or buffers.

The present pharmaceutical preparations, which, if desired, may also contain other pharmacologically valuable substances, are manufactured in a manner known per se, for example by means of conventional mixing and dissolving processes. The flowable powder obtained after grinding crystalline (5R,6S)-2-aminomethyl-6-[(1R)-1-hydroxyethyl]-2-penem-3-carboxylic acid and optionally additional carriers, such as mannitol, can also be introduced, by machine under aseptic conditions, directly into phials or ampoules in the desired quantities. The preparations of the present invention contain from approximately 0.1% to 100% active ingredient and preparations in ampoules from approximately 50% to 100%.

Depending on the type of infection and the condition of the individual infected organism, daily parenteral doses of from approximately 100 mg to approximately 5 g of active ingredient are used to treat warm-blooded animals (humans and animals) weighing approximately 70 kg.

The invention also relates to the use of the crystalline penem compound according to the invention for the therapeutic treatment of the human and animal body.

The following Examples serve to illustrate the invention. Temperatures are given in degrees Celcius.

EXAMPLE 1

1-[(3S,4R)-3-[(1R)-1-allyloxycarbonyloxyethyl]-4-(allyloxycarbonylaminoacetylthio)-2-oxoazetidin-1-yl]-2-triphenylphosphoranylideneacetic acid allyl ester To 0.385 g of the silver salt of 2-[(3S,4R)-3-[(1R)-1-allyloxycarbonyloxyethyl]-4-mercapto-2-oxoazetidin-1-yl]-2-triphenylphosphoranylideneacetic acid allyl ester in 10 ml of absolute methylene chloride there is added 0.5 ml of pyridine and then, at 0°, dropwise, a mixture of 0.13 g of allyloxycarbonylaminoacetyl chloride and 10 ml of absolute methylene chloride. After stirring for 30 minutes, the solid substance is filtered off over Hyflo and the filtrate is washed with aqueous $NaHCO_3$ solution and then with brine. After drying over $Na_2SO_4$, concentration is carried out in vacuo. The residue is purified by chromatography over silica gel (eluant: toluene/ethyl acetate 4:1).

IR ($CH_2Cl_2$) 3440; 1750; 1740; 1700; 1620 cm$^{-1}$.

The starting material, allyloxycarbonylaminoacetyl chloride, can be manufactured as follows:

(a) Allyloxycarbonylaminoacetic acid

At 0°, 12 ml of chloroformic acid allyl ester are added dropwise to a solution of 7.51 g of glycine in 20 ml of water and 44 ml of 5N NaOH solution. The suspension is then stirred for 16 hours at room temperature. After removing the insoluble material by filtration, the filtrate is diluted with 100 ml of water and washed twice with $CH_2Cl_2$. The aqueous phase is adjusted to pH 2 with 4N HCl and extracted twice with $CH_2Cl_2$. The combined organic extracts are washed once with brine, dried over $MgSO_4$ and concentrated by evaporation to form the white crystals of the title compound.

IR in $CH_2Cl_2$: 3450; 1715 cm$^{-1}$.

(ab) Allyloxycarbonylaminoacetyl chloride

At 0°, 5.7 ml of thionyl chloride are added to 3.18 g of allyloxycarbonylaminoacetic acid. The mixture is then stirred for 2 hours at the same temperature under a protective gas. The whole is then diluted with absolute toluene and concentrated in a rotary evaporator.

IR ($CH_2Cl_2$): 3435; 1800; 1725 cm$^{-1}$.

The silver salt of 2-[(3S,4R)-3-[(1R)-1-allyloxycarbonyloxyethyl]-4-mercapto-2-oxoazetidin-1-yl]-2-triphenylphosphoranylideneacetic acid allyl ester is manufactured as follows:

(ba) (2S,3R)-2-bromo-3-hydroxybutyric acid p-methoxybenzylamide

In the course of 20 minutes, 4.16 g of 1-hydroxybenzotriazole and 5.63 g of dicyclohexylcarbodiimide in 60 ml of THF are added dropwise to a solution, stirred at room temperature under an argon atmosphere, of 5 g of (2S,3R)-2-bromo-3-hydroxybutyric acid and 3.52 g of p-methoxybenzylamine in 60 ml of absolute THF. The reaction mixture is stirred for 48 hours, the dicyclohexylurea that precipitates is filtered off and washed several times with THF, and the filtrate is concentrated by evaporation. The resulting crude product contains dicyclohexylurea and hydroxybenzotriazole as impurities. After chromatography of the mixture over silica gel (system: toluene; toluene/ethyl acetate 1:4) and crystallisation of the pure fractions from methylene chloride/diethyl ether, the title compound having a melting point of 122°–124° is obtained.

$[\alpha] = -7 \pm 1°$ (1.112% in chloroform).

(bb) (2R,3R)-2,3-epoxybutyric acid p-methoxybenzylamide 50 ml of 50% NaOH solution and 456 mg (2 mmol) of benzyltriethylammonium chloride are added to a solution of 6.04 g (20 mmol) of (2S,3R)-2-bromo-3-hydroxybutyric acid p-methoxybenzylamide in 150 ml of methylene chloride. The two-phase mixture is stirred vigorously for 20 hours at room temperature. The organic layer is separated off and the aqueous phase is then extracted with methylene chloride. The combined methylene chloride solutions are dried and concentrated by evaporation. The resulting crude product is chromatographed over 40 times its weight of silica gel in the system methylene chloride/methanol (99:1). After crystallisation of the pure fractions from methylene chloride/diethyl ether/petroleum ether, the title compound, melting point 75°–76°, is obtained.

(bc) (2R,3R)-2,3-epoxybutyric acid N-tert.-butoxycarbonylmethyl-N-p-methoxybenzylamide A solution of 2.21 g of (2R,3R)-2,3-epoxybutyric acid p-methoxybenzylamide in 100 ml of THF is added dropwise to a mixture, stirred at 0° under an argon atmosphere, of 550 mg of sodium hydride dispersion (55–60% in oil) and 1.52 ml of bromoacetic acid tert.-butyl ester in 25 ml of THF. The reaction mixture is heated to room temperature and stirred for a further 1 hour (reaction monitored by thin-layer chromatography). Total reaction time: 90 minutes. The insoluble portions are filtered off and washed with THF and the combined filtrates are concentrated by evaporation. The resulting crude product is purified by chromatography over 150 g of silica gel (system: toluene, toluene/ethyl acetate 80:20). Concentration of the pure fractions by evaporation yields the amorphous title compound.

IR spectrum: bands inter alia at 1740; 1670; 1650; 1615; 1517; 1465; 1360 and 1035 cm$^{-1}$.

(bd) (3S,4S)-1-(p-methoxybenzyl)-3-[(1R)-1-hydroxyethyl]4-tert.-butoxycarbonyl-2-azetidinone 9.23 g of tetrabutylammonium fluoride trihydrate are left to stand for 16 hours at 5° with 40 g of molecular sieve (type 4171/16 - pre-dried at 300°) in 80 ml of THF. The mixture is cooled to 0°, a solution of 2.8 g of (2R,3R)-2,3-epoxybutyric acid N-tert.-butoxycarbonylmethyl-N-methoxybenzylamide in 20 ml of THF is added and the whole is stirred for 2 hours at 0°–5°. The molecular sieve is filtered off while washing with THF and the filtrate is applied directly to a column, prepared in toluene, containing 250 g of silica gel. The fractions, eluted with toluene/ethyl acetate (70:30 mixture) and concentrated by evaporation, are taken up in methylene chloride, washed twice, in succession, with 1N sulphuric acid, with saturated aqueous $NaHCO_3$ solution and with water, dried and concentrated by evaporation. After short-column chromatography over silica gel (toluene, toluene/ethyl acetate 60:40) and crystallisation from methylene chloride/diethyl ether/petroleum ether, the pure title compound, having a melting point of 85°–87°, is obtained.

(be) (3S,4S)-1-(p-methoxybenzyl)-3-[(1R)-1-allyloxycarbonyloxyethyl]-4-tert.-butoxycarbonyl-2-azetidinone At 0°, 24 ml of 1N NaOH, 820 mg of tetrabutylammonium bisulphate and 1 ml of chloroformic acid allyl ester are added to a solution of 2 g of (3S,4S)-1-(p-methoxybenzyl)-3-[(1R)-1-hydroxyethyl]-4-tert.-butoxycarbonyl-2-azetidinone in 24 ml of methylene chloride and the whole is stirred vigorously. After a reaction time of 20 and 40 minutes, further portions (each of 1 ml) of chloroformic acid allyl ester are added. The reaction mixture is diluted with methylene chloride, the aqueous phase is separated off and the organic layer is washed in succession with 5% aqueous citric acid and 8% aqueous $NaHCO_3$ solution and then dried and concentrated by evaporation. After purifying by chromatography, the pure, amorphous title compound is obtained.

IR spectrum: bands inter alia at 1765; 1745 (sh); 1615; 1593; 1515; 1160 and 1035 cm$^{-1}$.

(bf) (3S,4S)-1-(p-methoxybenzyl)-3-[(1R)-1-allyloxycarbonyloxyethyl]-4-carboxylic acid 2-azetidinone 1.6 g of (3S,4S)-1-(p-methoxybenzyl)-3-[(1R)-1-allyloxycarbonyloxyethyl]-4-tert.-butoxycarbonyl-2-azetidinone are dissolved at 0° in 10 ml of trifluoroacetic acid. After a reaction period of one hour at room temperature, the reaction mixture is concentrated by evaporation under a high vacuum and the resulting title compound is processed further without being purified.

$[\alpha] = +85 \pm 1°$ (1.0% in chloroform).

(bg) (3R,4R)-1-(p-methoxybenzyl)-3-[(1R)-1-allyloxycarbonyloxyethyl]-4-acetoxy-2-azetidinone 1.6 g of lead(IV) acetate (approximately 10% acetic acid content) are added to a solution, stirred at room temperature under an argon atmosphere, of 1.4 g of (3S,4S)-1-(p-methoxybenzyl)-3-[(1R)-1-allyloxycarbonyloxyethyl]-4-carboxylic acid 2-azetidinone in a mixture of 45 ml of THF and 6.6 ml of dimethylformamide and the whole is stirred for approximately 1 hour until the substrate has reacted completely. Excess oxidising agent is decomposed by adding 0.5 ml of ethylene glycol (10 minutes at room temperature). The lead(II) acetate that has precipitated is filtered off from the reaction mixture, the filter residue is washed with THF and the filtrate is concentrated by evaporation. The resulting oily residue is taken up in methylene chloride, washed twice, in succession, with saturated NaHCO₃ solution, water and saturated NaCl solution, dried and concentrated by evaporation. By chromatography of the residue over silica gel (toluene; toluene/ethyl acetate 90:10) the pure title compound is obtained.

$[\alpha] = +90° \pm 1°$ (1.0% in chloroform).

(bh) (3R,4R)-3-[(1R)-1-allyloxycarbonyloxyethyl]-4-acetoxy-2-azetidinone

At 10°, a solution of 5.37 g of cerium(IV) ammonium nitrate in 15 ml of water is added to a solution of 900 mg (1.18 mmol) of (3R,4R)-1-(p-methoxybenzyl)-3-[(1R)-1-allyloxycarbonyloxyethyl]-4-acetoxy-2-azetidinone in 30 ml of acetonitrile, and the whole is stirred for two hours at room temperature. After extraction with ethyl acetate, washing with saturated NaHCO₃ solution, drying of the organic phase over sodium sulphate and concentration by evaporation under reduced pressure, the crude title compound, which is purified by chromatography over silica gel using toluene/ethyl acetate (4:1 and 1:1), is obtained.

$[\alpha] = +84 \pm 1°$ (1.0% in chloroform).

(bi) (3S,4R)-3-[(1R)-1-allyloxycarbonyloxyethyl]-4-triphenylmethylthioazetidin-2-one 892 mg of triphenylmethylmercaptan are suspended at 0° in 5 ml of methanol and a total of 0.16 g of a 50% sodium hydride suspension in oil is added in portions thereto over a period of 10 mintues. A solution of 0.62 g of (3R,4R)-3-[(1R)-1-allyloxy carbonyl-oxyethyl]-4-acetoxyazetidin-2-one in 7 ml of acetone and 5 ml of water is then added dropwise thereto over a period of 15 minutes. After stirring for one hour at 0° and for a further three hours at room temperature, the reaction mixture is concentrated in a rotary evaporator and extracted with 20 ml of methylene chloride. The organic phase is washed with brine and dried over MgSO₄. After concentrating, the crude title compound is purified by chromatography over silica gel (eluant: toluene/ethyl acetate 19:1). TLC (toluene/ethyl acetate 4:1) $R_f = 0.3$, IR (CH₂Cl₂): 3400; 1770; 1745 cm⁻¹.

(bj) 2-[(3S,4R)-3-[(1R)-1-allyloxycarbonyloxyethyl]-4-triphenylmethylthio-2-oxoazetidin-1-yl]-2-hydroxyacetic acid allyl ester 4 g of molecular sieve (4Å) are added to 0.82 g of (3S,4R)-3-[(1R)-1-allyloxycarbonyloxyethyl]-4-triphenylmethylthioazetidin-2-one and 0.416 g of glyoxylic acid allyl ester ethyl hemiacetal in 10 ml of absolute toluene and the whole is stirred for 61hours at 60°. After filtering and concentrating in a rotary evaporator under reduced pressure, the title compound is obtained. TLC (silica gel; toluene/ethyl acetate 4:1), $R_f = 0.1$. IR (CH₂Cl₂) 3510; 1770; 1745 cm⁻¹.

(bk) 2-[(3S,4R)-3-[(1R)-1-allyloxycarbonyloxyethyl]-4-triphenylmethylthio-2-oxoazetidin-1-yl]-2-triphenylphosphoranylideneacetic acid allyl ester While stirring at 0°, 0.182 ml of thionyl chloride and 0.206 ml of pyridine are added in succession within 5 minutes to a solution of 1 g of 2-[(3S,4R)- 3-[(1R)-1-allyloxycarbonyloxyethyl]-4-triphenylmethylthio-2-oxoazetidin-1-yl]-2-hydroxyacetic acid allyl ester in 10 ml of tetrahydrofuran. This white suspension is stirred at 0° for 30 minutes and filtered over Hyflo. After washing the residue with toluene, concentration is carried out in a rotary evaporator. The residue is dissolved in 10 ml of dioxan, 0.624 g of triphenylphosphine and 0.257 ml of lutidine are added and the whole is stirred for 46 hours at a bath temperature of 80°. The mixture is filtered over Hyflo and the residue is washed with toluene. The combined filtrates are concentrated by evaporation, and chromatography of the residue over silica gel yields the pure product (eluant toluene/ethyl acetate 19:1 to 4:1), TLC (silica gel; toluene/ethyl acetate 4:1), $R_f = 0.24$, IR (CH₂Cl₂) 1745; 1620 cm⁻¹.

(bl) Silver salt of 2-[(3S,4R)-3-[(1R)-1-allyloxycarbonyloxyethyl]-4-triphenylmethylthio-2-oxoazetidin-1-yl]-2-triphenylphosphoranylideneacetic acid allyl ester 0.46 g of 2-[(3S,4R)-3-[(1R)-1-allyloxycarbonyloxyethyl]-4-triphenylmethylthio-2-oxoazetidin-1-yl]-2triphenylphosphoranylideneacetic acid allyl ester are placed in 6 ml of diethyl ether and at room temperature 4.4 ml of a 0.5M aqueous silver nitrate solution are added thereto. 0.077 ml of triethylamine are then added thereto and the reaction mixture is then stirred for 30 minutes. The solid material is filtered off with suction and washed well with water and diethyl ether. The residue is again suspended in 300 ml of water and 300 ml of diethyl ether, stirred and then filtered off. After washing again with diethyl ether, the solid material is dried under a high vacuum.

IR (CH₂Cl₂): 1760; 1745; 1630 cm⁻¹.

EXAMPLE 2

(5R,6S)-2-allyloxycarbonylaminomethyl-6-[(1R)-1-allyloxycarbonyloxyethyl]-2-penem-3-carboxylic acid allyl ester A solution of 2.42 g of 2-[(3S,4R)-3-[(1R)-1-allyloxycarbonyloxyethyl]-4-(allyloxycarbonylaminoacetylthio)-2-oxoazetidin-1-yl]-2-triphenylphosphoranylideneacetic acid allyl ester in 300 ml of absolute toluene is stirred under an argon atmosphere for 24 hours at the reflux temperature. The solvent is then concentrated by evaporation and the crude product is purified by chromatography over silica gel. (Eluant: toluene/ethyl acetate 9:1)

IR (CH₂Cl₂): 3435; 1790; 1740; 1720; 1580 cm⁻¹.

EXAMPLE 3

Amorphous (5R,6S)-2-aminomethyl-6-[(1R)-1-hydroxyethyl]-2-penem-3-carboxylic acid Variant A:

A solution of 100 mg (0.22 mmol) of (5R,6S)-2-allyloxycarbonylaminomethyl-6-[(1R)-1-allyloxycarbonyloxyethyl]-2-penem-3-carboxylic acid allyl ester, 308 mg (2.2 mmol) of dimedone and 30 mg (0.11 mmol) of triphenylphosphine in 4 ml of tetrahydrofuran is flushed for 5 minutes with argon. 22 mg (0.019 mmol) of tetrakis-triphenylphosphine-palladium are then added at room temperature. After 5 minutes a precipitate begins to form. The suspension is stirred for a total of 1 hour at room temperature under argon. The product that has precipitated is filtered off, washed with tetrahydrofuran, ethyl acetate and hexane, and dried under a high vacuum.

TLC (H₂O, OPTI UPC₁₂), $R_f=0.48$.

Variant B:

A solution of 100 mg (0.22 mmol) of (5R,6S)-2-allyloxycarbonylaminomethyl- 6-[(1R)-1-allyloxycarbonyloxyethyl]-2-penem-3-carboxylic acid allyl ester, 0.23 ml (2.2 mmol) of acetyl acetone and 30 mg (0.11 mmol) of triphenylphosphine in 2 ml of tetrahydrofuran is flushed with argon for 5 minutes. 20 mg (0.017 mmol) of tetrakis-triphenylphosphine-palladium are then added at room temperature. After 5 minutes a precipitate forms. After a total reaction time of 45 minutes the precipitate is filtered off, washed with tetrahydrofuran and diethylether and dried under a high vacuum.

TLC (H₂O, OPTI UPC₁₂), $R_f=0.48$.

Variant C:

A solution of 100 mg (0.22 mmol) of (5R,6S)-2-allyloxycarbonylaminomethyl-6-[(1R)-1-allyloxycarbonyloxyethyl]-2-penem-3-carboxylic acid allyl ester, 123 mg (0.88 mmol) of dimedone and 30 mg (0.11 mmol) of triphenylphosphine in 2 ml of tetrahydrofuran is flushed for 5 minutes with argon. 22 mg (0.019 mmol) of tetrakis-triphenylphosphine-palladium are then added at room temperature. After 1 hour the precipitate is filtered off, washed with tetrahydrofuran and diethyl ether and dried under a high vacuum.

TLC (H₂O, OPTI UPC₁₂), $R_f=0.48$.

Variant D:

A solution of 100 mg (0.22 mmol) of (5R,6S)-2-allyloxycarbonylaminomethyl-6-[(1R)-1-allyloxycarbonyloxyethyl]-2-penem-3-carboxylic acid allyl ester and 123 mg (0.88 mmol) of dimedone in 2 ml of tetrahydrofuran is flushed for 5 minutes with argon. 22 mg (0.019 mmol) of tetrakis-triphenylphosphinepalladium are then added at room temperature. After 1 hour the precipitate is filtered off, washed with tetrahydrofuran and diethyl ether and dried under a high vacuum.

TLC (H₂O, OPTI UPC₁₂), $R_f=0.48$.

Variant E:

A solution of 100 mg (0.22 mmol) of (5R,6S)-2-allyloxycarbonylaminomethyl-6-[(1R)-1-allyloxycarbonyloxyethyl]-2-penem-3-carboxylic acid allyl ester and 123 mg (0.88 mmol) of dimedone in 2 ml of ethyl acetate is flushed for 5 minutes with argon. 22 mg (0.019 mmol) of tetrakis-triphenylphosphine-palladium are then added at room temperature. After 1 hour the precipitate is filtered off, washed with ethyl acetate and diethyl ether and dried under a high vacuum.

TLC (H₂O, OPTI UPC₁₂), $R_f=0.48$).

Variant F:

A solution of 100 mg (0.22 mmol) of (5R,6S)-2-allyloxycarbonylaminomethyl-6-[(1R)-1-allyloxycarbonyloxyethyl]-2-penem-3-carboxylic acid allyl ester and 0.05 ml (0.88 mmol) of glacial acetic acid in 2 ml of tetrahydrofuran is flushed for 5 minutes with argon. 22 mg (0.019 mmol) of tetrakis-triphenylphosphinepalladium are then added at room temperature. After 1 hour the precipitate is filtered off, washed with tetrahydrofuran and diethyl ether and dried under a high vacuum.

TLC (H₂O, OPTI UPC₁₂), $R_f=0.48$.

Variant G:

A solution of 100 mg (0.22 mmol) of (5R,6S)-2-allyloxycarbonylaminomethyl-6-[(1R)-1-allyloxycarbonyloxyethyl]-2-penem-3-carboxylic acid allyl ester and 123 mg (0.88 mmol) of dimedone in 4 ml of methylene chloride is flushed for 5 minutes with argon. 22 mg (0.019 mmol) of tetrakis-triphenylphosphine-palladium are then added at room temperature and stirred further at room temperature. TLC tests show a very slow reaction. After 15 hours the precipitate is filtered off. The latter is washed with methylene chloride and dried under a high vacuum.

TLC (H₂O, OPTI UPC₁₂), $R_f=0.48$.

Variant H:

A solution of 100 mg (0.22 mmol) of (5R,6S)-2-allyloxycarbonylaminomethyl-6-[(1R)-1-allyloxycarbonyloxyethyl]-2-penem-3-carboxylic acid allyl ester and 62 mg (0.44 mmol) of dimedone in 2 ml of tetrahydrofuran is flushed for 5 minutes with argon. 22 mg (0.019 mmol) of tetrakis-triphenylphosphinepalladium are then added at room temperature. After 1 hour the precipitate is filtered off, washed with tetrahydrofuran and ethyl acetate and dried under a high vacuum.

TLC (H₂O, OPTI UPC₁₂), $R_f=0.48$.

Variant I:

A solution of 100 mg (0.22 mmol) of (5R,6S)-2-allyloxycarbonylaminomethyl-6-[(1R)-1-allyloxycarbonyloxyethyl]-2-penem-3-carboxylic acid allyl ester and 62 mg (0.44 mmol) of dimedone in 2 ml of tetrahydrofuran is flushed for 5 minutes with argon. 5 mg (0.0043 mmol) of tetrakis-triphenylphosphinepalladium are then added at room temperature. After 1 hour the precipitate is filtered off, washed with tetrahydrofuran and diethyl ether and dried under a high vacuum.

TLC (H₂O, OPTI UPC₁₂), $R_f=0.48$.

Variant J:

A solution of 100 mg (0.22 mmol) of (5R,6S)-2-allyloxycarbonylaminomethyl-6-[(1R)-1-allyloxycarbonyloxyethyl]-2-penem-3-carboxylic acid allyl ester and 123 mg (0.88 mmol) of dimedone in 2 ml of ethanol is flushed for 5 minutes with argon. 10 mg (0.0086 mmol) of tetrakis-triphenylphosphine-palladium are then added at room temperature. After 7 hours the precipitate is filtered off, washed with tetrahydrofuran and diethyl ether and dried under a high vacuum.

TLC (H₂O, OPTI UPC₁₂), $R_f=0.48$.

Variant K:

A solution of 11.3 g (25 mmol) of (5R,6S)-2-allyloxycarbonylaminomethyl-6-[(1R)-1-allyloxycarbonyloxyethyl]-2-penem-3-carboxylic acid allyl ester and 7.7 g (55 mmol) of dimedone in 220 ml of tetrahydrofuran is flushed for 10 minutes with argon and then 1.1 g (0.952 mmol) of tetrakis-triphenylphosphine-palladium are added. The solution heats up slightly (approximately 30° C.) and after approximately 5 minutes a precipitate starts to form. After 1 hour 0.2 ml (2.1 mmol) of methallyl chloride is added and the whole is stirred for a further 15 minutes. The precipitate is then filtered off, washed with tetrahydrofuran and ethyl acetate and the solid residue is dried under a high vacuum. The residue is amorphous.

TLC (H₂O, OPTI UPC₁₂); $R_f=0.48$.

EXAMPLE 4

Manufacture of crystalline (5R,6S)-2-aminomethyl-6-[(1R)-1-hydroxyethyl]-2-penem-3-carboxylic acid Variant A: (water-containing ethanol)

20.4 g of amorphous (5R,6S)-2-aminomethyl-6-[(1R)-1-hydroxyethyl]-2-penem-3-carboxylic acid (see Example 3) are dissolved in 300 ml of twice-distilled water at 30°. The aqueous solution is cooled to 5°, 1 g of activated carbon is added and the whole is stirred for 15 minutes and then filtered until clear. The clear filtrate is concentrated completely under a high vacuum and the residue is suspended in 190 ml of ethanol (96%). The suspension is stirred vigorously at room temperature for 30 minutes. The white crystals (needles) are filtered off and washed with ethanol (96%). The product is dried for 16 hours at 20° under a high vacuum (13 Pa).

Melting point 165° (decomposition); TLC (H$_2$O, OPTI UPC$_{12}$) R$_f$=0.48; $\alpha_D^{20}$ (0.64% in H$_2$O) +161.9°+1.6°; UV (H$_2$O) $\lambda_{max}$ 311 nm ($\xi$5100); IR (DMSO-d$_6$): 3431, 2970, 1774, 1628, 1574 cm$^{-1}$; $^1$H-NMR (360 MHz, D$_2$O): $\delta$=1.35 (d, CH$_3$), 4.02 (dd, CH-CO), 4.07 (AB, CH$_2$), 4.28 (m, C$\underline{H}$-CH$_3$), 5.74 ppm (d, CH-N).

C$_9$H$_{12}$N$_2$O$_4$S.0.79 H$_2$O (molecular weight 258.5)

|   | calculated | found |
|---|---|---|
| C | 41.81 | 42.33 |
| H | 5.32 | 5.29 |
| N | 10.83 | 10.76 |
| S | 12.40 | 12.52 |
| H$_2$O | 5.52 | 5.52 |

X-ray powder pattern of crystalline (5R,6S)-2-aminomethyl-6-[(1R)-1-hydroxyethyl]-2-penem-3-carboxylic acid In order to determine the lattice plane spacings (d-values) the diffraction pattern was recorded on film. A Guinier camera (Enraf-Nonius FR 552) with copper-k$_{\alpha 1}$ radiation (wave length=1.54050 Å) was used for the recording. Quartz was used as the calibrating substance, the d-values thereof being calculated from a=4.913 Å and c=5.405 Å (PDF 5-490).

In the following Table the d-values of the strongest lines having d-values of over 3.0 Ångstrom are indicated together with the relative line intensities estimated by eye.

| d-values (Ångstrom) | relative intensity |
|---|---|
| 10.9 | very strong |
| 10.0 | medium |
| 9.7 | medium |
| 7.9 | strong |
| 7.3 | strong |
| 7.0 | strong |
| 6.7 | weak |
| 6.3 | very strong |
| 5.90 | very weak |
| 5.85 | very weak |
| 5.60 | very weak |
| 5.53 | very weak |
| 5.44 | very weak |
| 5.33 | very weak |
| 5.01 | very weak |
| 4.93 | weak |
| 4.64 | very weak |
| 4.58 | very weak |
| 4.53 | strong |
| 4.42 | very weak |
| 4.34 | very strong |
| 4.28 | very weak |
| 4.23 | very weak |
| 4.10 | strong |
| 4.05 | very weak |
| 3.99 | medium |
| 3.91 | weak |
| 3.82 | medium |
| 3.78 | medium |
| 3.73 | strong |
| 3.65 | medium |
| 3.59 | strong |
| 3.54 | medium |
| 3.42 | strong |
| 3.36 | medium |
| 3.29 | strong |
| 3.20 | medium |
| 3.13 | medium |
| 3.11 | strong |
| 3.03 | medium |
| 3.00 | medium |

Variant B (water-containing n-propanol)

8.2 g of amorphous (5R,6S)-2-aminomethyl-6-[(1R)-1-hydroxyethyl]-2-penem-3-caboxylic acid are dissolved in 120 ml of twice-distilled water at 30°. The aqueous solution is cooled to 5°, 0.5 g of activated carbon is added, the whole is stirred for 15 minutes and then filtered until clear. The clear filtrate is concentrated completely under a high vacuum and the residue is suspended in 80 ml of n-propanol (92%). The suspension is stirred vigorously for 30 minutes at room temperature. The white needles are filtered off and washed with n-propanol (92%). The product is dried for 15 hours at 20° under a high vacuum (14 Pa).

melting point 165° (decomposition); TLC (H$_2$O, OPTI UPC$_{12}$) R$_f$=0.48.

C$_9$H$_{12}$N$_2$O$_4$S.0.28 H$_2$O (molecular weight 249.4)

|   | calculated | found |
|---|---|---|
| C | 43.30 | 43.46 |
| H | 5.03 | 4.99 |
| N | 11.22 | 11.27 |
| S | 12.83 | 12.90 |
| H$_2$O | 2.05 | 2.05 |

Apart from slight differences in the estimated line intensities of some lines, the X-ray powder pattern of the substance is completely identical with the X-ray powder pattern described under Variant A.

Variant C (water-containing 2-butanol)

14.9 g of amorphous (5R,6S)-2-aminomethyl-6-[(1R)-1-hydroxyethyl]-2-penem-3-carboxylic acid are dissolved in 210 ml of twice-distilled water at 30°. The aqueous solution is cooled to 5°, 0.7 g of activated carbon is added, and the whole is stirred for 15 minutes and then filtered until clear. The clear filtrate is concentrated completely under a high vacuum and the residue is suspended in 140 ml of 2-butanol (90%). The suspension is stirred vigorously for 30 minutes at room temperature. The white crystals (needles) are filtered off and washed with 2-butanol (90%). The product is dried for 16 hours at 20° under a high vacuum (13 Pa).

melting point 165° C. (decomposition); TLC (H$_2$O, OPTI UPC$_{12}$) R$_f$=0.48.

C$_9$H$_{12}$N$_2$O$_4$S.1.21 H$_2$O (molecular weight 266.06)

|   | calculated | found |
|---|---|---|
| C | 40.63 | 40.78 |
| H | 5.49 | 5.53 |
| N | 10.53 | 10.43 |
| S | 12.05 | 11.53 |
| H$_2$O | 8.19 | 8.19 |

Apart from slight differences in the estimated line intensities of some lines, the X-ray powder pattern of the substance is completely identical with the X-ray powder pattern described under Variant A.

EXAMPLE 5

Determination of the thermal stability

In order to determine the thermal stability, samples of crystalline (5R,6S)-2-aminomethyl-6-[(1R)-1-hydroxyethyl)-2-penem-3-carboxylic acid and amorphous racemic (5R,6S,1'R and 5S,6R,1'S)-2-aminomethyl-6-(1'-hydroxyethyl)-2-penem-3-carboxylic acid previously known from German Offenlegungsschrift No. 2 950 898 are used.

20 mg samples are weighed in glass tubes. The glass tubes are sealed firmly with PVC stoppers and heated in a thermostatted oil bath at 50°. At regular intervals individual glass tubes are removed from the oil bath, the samples are dissolved in 100 ml of doubly distilled water and the penem content is determined by means of HPLC analysis [UV detector: Kratos, 305 nm; injection machine: Wisp; 20 μl charge; integrator: Shimazu, C-R3A; pump: Altex, 2.0 ml/minute; column: Knauer, 25 cm×4 mm, $C_{18}$/10 um; eluant: acetonitrile/water 2:98, pH5].

The following values were obtained (Sample A: crystalline (5R,6S)-2-aminomethyl-6-[(1R)-1-hydroxyethyl]-2-penem-3-carboxylic acid; Sample B: amorphous (5R,6S,1'R and 5S,6R,1'S)-2-aminomethyl-6-(1'-hydroxyethyl)-2-penem-3-carboxylic acid):

|  | Penem content (%) | |
| --- | --- | --- |
| Day | Sample A | Sample B |
| 0 | approx. 100 | approx. 100 |
| 1.8 | 99 | 84 |
| 3 | 98 | 78 |
| 4.5 | 97 | 73 |
| 7 | 95 | 67 |
| 9 | 94 | 64 |
| 12 | 92 | 63 |
| 14 | 91 | 62 |

The crystalline compound thus has considerably greater long-term stability under the action of heat than does the previously known amorphous product.

EXAMPLE 6

Dry-filled ampoules or phials, containing crystalline (5R,6S)-2-aminomethyl-6-[(1R)-1-hydroxyethyl]-2-penem-3-carboxylic acid as active ingredient, are manufactured as follows:

| Composition (for 1 ampoule or phial): | |
| --- | --- |
| active ingredient (without water) | 0.5 g |
| mannitol | 0.05 g |

The active substance and the mannitol are weighed off under aseptic conditions and introduced into 10 ml ampoules or 10 ml phials, and the ampoules or phials are sealed and tested.

I claim:

1. (5R,6S)-2-aminomethyl-6-[(1R)-1-hydroxyethyl]-2-penem-3-carboxylic acid in crystalline form.

2. (5R,6S)-2-aminomethyl-6-[(1R)-1-hydroxyethyl]-2-penem-3-carboxylic acid in crystalline form according to claim 1, obtainable by the crystallisation of (5R,6S)-2-aminomethyl-6-[(1R)-1-hydroxyethyl]-2-penem-3-carboxylic acid from a supersaturated solution in a water-containing organic solvent.

3. Crystalline (5R,6S)-2-aminomethyl-6-[(1R)-1-hydroxyethyl]-2-penem-3-carboxylic acid according to claim 1, characterised by the following lattice spacings (d-values) and relative line intensities of its X-ray powder pattern (camera according to Guinier, radiation source: copper-$K_{\alpha 1}$):

| d-values (Ångstrom) | relative intensity |
| --- | --- |
| 10.9 | very strong |
| 10.0 | medium |
| 9.7 | medium |
| 7.9 | strong |
| 7.3 | strong |
| 7.0 | strong |
| 6.7 | weak |
| 6.3 | very strong |
| 5.90 | very weak |
| 5.85 | very weak |
| 5.60 | very weak |
| 5.53 | very weak |
| 5.44 | very weak |
| 5.33 | very weak |
| 5.01 | very weak |
| 4.93 | weak |
| 4.64 | very weak |
| 4.58 | very weak |
| 4.53 | strong |
| 4.42 | very weak |
| 4.34 | very strong |
| 4.28 | very weak |
| 4.23 | very weak |
| 4.10 | strong |
| 4.05 | very weak |
| 3.99 | medium |
| 3.91 | weak |
| 3.82 | medium |
| 3.78 | medium |
| 3.73 | strong |
| 3.65 | medium |
| 3.59 | strong |
| 3.54 | medium |
| 3.42 | strong |
| 3.36 | medium |
| 3.29 | strong |
| 3.20 | medium |
| 3.13 | medium |
| 3.11 | strong |
| 3.03 | medium |
| 3.00 | medium |

4. Process for the manufacture of crystalline (5R,6S)-2-aminomethyl-6-2-penem-3-carboxylic acid, characterised in that (5R,6S)-2- (5R,6S)-2-aminomethyl-6-[(1R)-1-hydroxyethyl]-2-penem-3-carboxylic acid is caused to crystallise from a supersaturated solution in a water-containing organic solvent and the product is collected and dried.

5. Process according to claim 4, characterised in that the water-containing organic solvent is a mixture of water and a water-miscible organic solvent, selected from the group consisting of lower alkanols having from 1 to 4 carbon atoms, glycols having from 1 to 4 carbon atoms and their mono- and di-($C_1$-$C_2$)-alkyl ethers.

6. Process according to claim 5, characterised in that the water-containing organic solvent is a mixture consisting of water and one of the water-miscible organic solvents mentioned in claim 5, the water content being from 2 to 20%.

7. Process according to claim 5, characterised in that the water-containing organic solvent is a mixture consisting of water and a lower alkanol having from 1 to 4 carbon atoms, the water content being from 2 to 20%

8. Process according to claim 5, characterised in that the water-containing organic solvent is 96% ethanol.

9. Process according to claim 4, characterised in that (5R,6S)-2-aminomethyl-6-[(1R)-1-hydroxyethyl]-2- penem-3-carboxylic acid is dissolved in a watercontaining organic solvent at room temperature or at elevated temperature of up to 50° C. and the supersaturation of the solution is effected by cooling the solution to from 0° to 20° C.

10. Process according to claim 4, characterised in that (5R,6S)-2-aminomethyl-6-[(1R)-1-hydroxyethyl]-2-penem-3-carboxylic acid is digested while stirring in one of the organic solvents having a water content of from 2 to 10% mentioned in claim 5.

11. Method for the treatment of bacterial infections in mammals, characterised in that the said mammal is administered a therapeutically effective dose of the compound according to claim 1.

12. An antibacterial pharmaceutical preparation comprising an antibacterially effective amount of (5R,6S)-2-aminomethyl-6-[(1R)-1-hydroxyethyl]-2-penem-3-carboxylic acid in crystalline form and a pharmaceutically acceptable carrier.

* * * * *